United States Patent [19]

Stroech et al.

[11] Patent Number: 4,925,865
[45] Date of Patent: * May 15, 1990

[54] ANTIMYCOTIC AGENTS

[75] Inventors: Klaus Stroech, Solingen; Monika Frie, Odenthal; Thomas Himmler, Cologne; Manfred Plempel, Haan, all of Fed. Rep. of Germany

[73] Assignee: Bayer Aktiengesellschaft, Leverkusen, Fed. Rep. of Germany

[*] Notice: The portion of the term of this patent subsequent to May 15, 2004 has been disclaimed.

[21] Appl. No.: 246,729

[22] Filed: Sep. 20, 1988

[30] Foreign Application Priority Data

Sep. 25, 1987 [DE] Fed. Rep. of Germany ....... 3732385

[51] Int. Cl.$^5$ .................... A61K 31/41; C07D 249/08
[52] U.S. Cl. .................. 514/383; 548/266.4; 548/267.8
[58] Field of Search .............. 548/262; 514/383

[56] References Cited

U.S. PATENT DOCUMENTS 4,507,140 3/1985 Sugavanan .................... 514/383
4,548,945 10/1985 Holmwood et al. ............ 514/383

FOREIGN PATENT DOCUMENTS 0040345 5/1981 European Pat. Off. .
0143379 6/1985 European Pat. Off. .
0180850 5/1986 European Pat. Off. .
3018865 11/1981 Fed. Rep. of Germany ...... 514/383
2129000 5/1984 United Kingdom ............ 548/262

OTHER PUBLICATIONS

Blume et al., "Preparation of α-Cyclopropyl, etc", CA 108:94558m (1988).

Primary Examiner—Richard L. Raymond
Assistant Examiner—Patricia L. Morris
Attorney, Agent, or Firm—Sprung Horn Kramer & Woods

[57] ABSTRACT

Combating mycoses in humans and other animals with hydroxyalkyl-azolyl derivatives of the formula

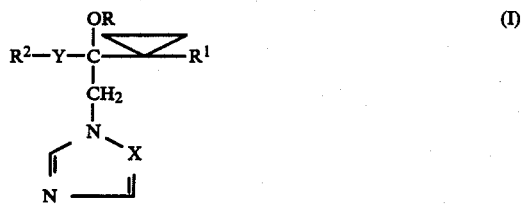

in which R stands for hydrogen, alkyl or acyl,
$R^1$ stands for halogen, optionally substituted phenyl or the $-Z-R^3$ grouping,
$R^2$ stands for optionally substituted alkyl, optionally substituted cycloalkyl, optionally substituted naphthyl, for the radical of the formula

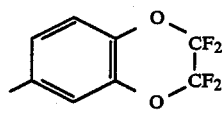

or for the radical of the formula

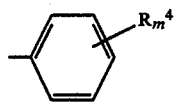

X stands for nitrogen or a CH group and
Y stands for the $-CH_2-CH_2-$, $-CH=CH-$, $-C\equiv C-$,

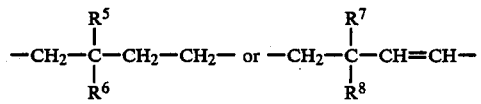

groupings, wherein $R^5$, $R^6$, $R^7$ and $R^8$ independently of one another stand for hydrogen or alkyl having 1 to 4 carbon atoms, and their acid addition salts.

6 Claims, No Drawings

ANTIMYCOTIC AGENTS

The present invention relates to hydroxyalkyl-azolyl derivatives and their pharmacologically tolerable acid addition salts for the treatment of diseases, in particular mycoses.

It has already been disclosed that certain azolylmethyl-cyclopropyl-carbinol derivatives, such as, for example, 1-(4-chlorophenyl)-1-(1-fluoro-cycloprop-1-yl)-2-(1,2,4-triazol-1-yl)-ethan-1-ol and 1-(4-chlorophenyl)-1-[1-(2,4-dichlorophenoxy)-cycloprop-1-yl]-2-(1,2,4-triazol-1-yl)-ethan-1-ol exhibit antimycotic properties (compare EP-OS No.0,180,850). However, the action of these substances is not always completely satisfactory in all indication areas. It has been found that the new hydroxyalkylazolyl derivatives of the formula

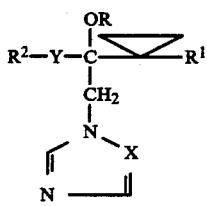

in which

R stands for hydrogen, alkyl or acyl, $R^1$ stands for halogen, optionally substituted phenyl or the $-Z-R^3$ grouping, wherein Z stands for oxygen, sulphur, SO or $SO_2$ and $R^3$ stands for optionally substituted alkyl, optionally substituted phenyl or optionally substituted phenylalkyl, $R^2$ stands for optionally substituted alkyl, optionally substituted cycloalkyl, optionally substituted naphthyl, for the radical of the formula

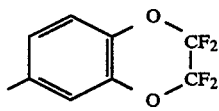

or for the radical of the formula

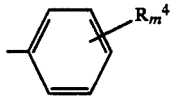

wherein $R^4$ stands for halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 halogen atoms, halogenoalkoxy having 1 or 2 carbon atoms and 1 to 5 halogen atoms, halogenoalkylthio having 1 or 2 carbon atoms and 1 to 5 halogen atoms, phenyl which is optionally substituted by alkyl having 1 or 2 carbon atoms and/or halogen, for phenoxy which is optionally substituted by alkyl having 1 or 2 carbon atoms and/or halogen, or for nitro, amino, alkylamino, dialkylamino, arylamino or alkylcarbonylamino and m stands for the numbers 0, 1, 2 or 3, X stands for nitrogen or a CH group and Y stands for the $-CH_2-CH_2-$, $-CH=CH-$, $-C\equiv C-$,

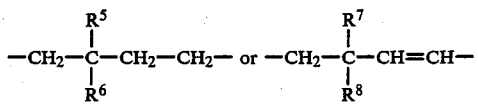

wherein $R^5$, $R^6$, $R^7$ and $R^8$ independently of one another stand for hydrogen or alkyl having 1 to 4 carbon atoms, and their acid addition salts possess good antimicrobial, in particular antimycotic, properties.

The substances to be used according to the invention contain an asymmetrical substituted carbon atom. They can therefore occur in optical isomeric forms. Moreover, those substances of the formula (I) in which Y stands for a $-CH=CH-$ group or for a

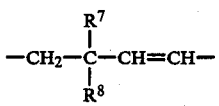

group can also occur in the form of cis or trans isomers. The invention relates both to the individual isomers and to their mixtures.

Formula (I) provides a general definition of the hydroxyalkyl-azolyl derivatives to be used according to the invention. In this formula, R preferably stands for hydrogen, alkyl having 1 to 6 carbon atoms or alkylcarbonyl having 1 to 6 carbon atoms in the alkyl part, $R^1$ preferably stands for fluorine, chlorine, bromine, for phenyl which is optionally substituted by halogen, halogenoalkyl having 1 or 2 carbon atoms and 1 to 5 halogen atoms, alkyl having 1 to 4 carbon atoms and/or alkoxy having 1 to 4 carbon atoms, or for the $-Z-R^3$ grouping, wherein Z stands for oxygen, sulphur, SO or $SO_2$ and $R^3$ stands for alkyl having 1 to 6 carbon atoms which is optionally substituted by alkoxy having 1 to 4 carbon atoms, alkylthio having 1 to 4 carbon atoms, phenyl and/or halogen, for phenyl which is optionally substituted by a substituent from the series comprising halogen, halogenoalkyl having 1 or 2 carbon atoms and 1 to 5 halogen atoms, alkyl having 1 to 4 carbon atoms and/or alkoxy having 1 to 4 carbon atoms, or for benzyl which is optionally substituted in the phenyl part by halogen, halogenoalkyl having 1 or 2 carbon atoms and 1 to 5 halogen atoms, alkyl having 1 to 4 carbon atoms and/or alkoxy having 1 to 4 carbon atoms, $R^2$ preferably stands for alkyl having 1 to 6 carbon atoms which is optionally substituted by alkoxy having 1 to 4 carbon atoms, alkylthio having 1 to 4 carbon atoms, phenyl and/or halogen, for cycloalkyl having 3 to 8 carbon atoms which is optionally substituted by alkyl having 1 to 4 carbon atoms and/or halogen, for naphthyl which is optionally substituted by alkyl having 1 to 4 carbon atoms and/or halogen, for the radical of the formula

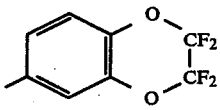

or for the radical of the formula

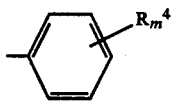

wherein
R$^4$ stands for fluorine, chlorine, bromine, methyl, ethyl, isopropyl, tert.-butyl, methoxy, methylthio, trifluoromethyl, trifluoromethoxy, trifluoromethylthio, phenyl which is optionally substituted by fluorine, chlorine and/or methyl, for phenoxy which is optionally substituted by fluorine, chlorine and/or methyl, or for nitro, amino, alkylamino having 1 to 4 carbon atoms in the alkyl group, dialkylamino having 1 to 4 carbon atoms in each alkyl group, phenylamino, or for alkylcarbonylamino having 1 to 4 carbon atoms in the alkyl group and m stands for the numbers 0, 1, 2 or 3, X preferably stands for nitrogen or a CH group and Y stands fro the —CH$_2$—CH$_2$—, —CH=CH—, —C≡C—,

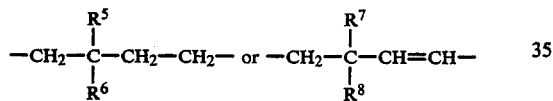

groupings,
wherein R$^5$, R$^6$, R$^7$ and R$^8$ independently of one another stand for hydrogen, methyl or ethyl.

When m stands for the numbers 2 or 3, the radicals standing for R$^4$ can be identical or different.

Particularly preferred compounds of the formula (I) are those in which
R stands for hydrogen, methyl, ethyl, n-propyl, isopropyl, n-butyl, isobutyl, methylcarbonyl, ethylcarbonyl, n-propylcarbonyl, isopropylcarbonyl, n-butylcarbonyl and isobutylcarbonyl, R$^1$ stands for fluorine, chlorine, bromine, phenyl which is optionally monosubstituted, disubstituted or trisubstituted by identical or different, fluorine, chlorine, bromine, trifluoromethyl, methyl, ethyl, methoxy and/or ethoxy substituents or stands for the grouping of the formula —Z—R$^3$,
wherein
Z stands for oxygen, sulphur, SO or SO$_2$ and
R$^3$ stands for methyl, ethyl, n-propyl, isopropyl, n-butyl, isobutyl or tert.-butyl, where each of these radicals can be monosubstituted, disubstituted or trisubstituted by identical or different methoxy, ethoxy, methylthio, phenyl, fluorine, chlorine and/or bromine substituents, or
R$^3$ stands for phenyl which is optionally monosubstituted, disubstituted or trisubstituted by identical or different fluorine, chlorine, bromine, trifluoromethyl, methyl, ethyl, methoxy and/or ethoxy substituents, or R$^3$ stands for benzyl which can be optionally monosubstituted, disubstituted or trisubstituted in the phenyl part by identical or different fluorine, chlorine, bromine, trifluoromethyl, methyl, ethyl, methoxy and/or ethoxy substituents, R$^2$ stands for alkyl having 1 to 4 carbon atoms which is optionally monosubstituted, disubstituted or trisubstituted by identical or different methoxy, ethoxy, methylthio, ethylthio, phenyl, fluorine, chlorine and/or bromne substituents, furthermore for cycloalkyl having 3 to 7 carbon atoms which is optionally monosubstituted, disubstituted or trisubstituted by identical or different methyl, ethyl, fluorine and/or chlorine substituents, additionally for naphthyl which is optionally monosubstituted, disubstituted or trisubstituted by identical or different methyl, fluorine and/or chlorine substituents or for the radical of the formula

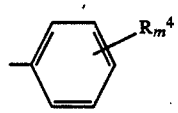

wherein
R$^4$ stands for fluorine, chlorine, bromine, methyl, ethyl, isopropyl, tert.-butyl, methoxy, methylthio, trifluoromethyl, trifluoromethoxy, trifluoromethylthio, phenyl which is optionally substituted by fluorine, chlorine and/or methyl, or for phenoxy which is optionally substituted by fluorine, chlorine and/or methyl, or stands for nitro, amino, alkylamino having 1 or 2 carbon atoms in the alkyl group, dialkylamino having 1 or 2 carbon atoms in each alkyl group, phenylamino or for alkylcarbonylamino having 1 or 2 carbon atoms in the alkyl group, m stands for the numbers 0, 1, 2 or 3, X stands for nitrogen or a CH group and Y stands for the —CH$_2$—CH$_2$—, —CH=CH—, —C≡C—,

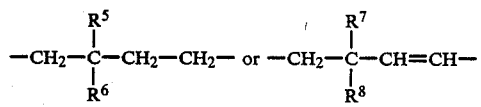

groupings,
wherein R$^5$, R$^6$, R$^7$ and R$^8$ independently of one another stand for hydrogen, methyl or ethyl.

Preferred compounds according to the invention are also pharmacologically tolerable addition products of acids and those hydroxyalkyl-azolyl derivatives of the formula (I), in which R, R$^1$, R$^2$, X and Y have the meanings which have already been preferably mentioned for these radicals.

The acids which can be adducted preferably include hydrohalic acids, such as, for example, hydrochloric acid and hydrobromic acid, in particular hydrochloric acid, furthermore phosphoric acid, nitric acid, sulphuric acid, mono- and bifunctional carboxylic acids and hydroxycarboxylic acids, such as, for example, acetic acid, maleic acid, succinic acid, fumaric acid, tartaric acid, citric acid, salicylic acid, sorbic acid and lactic acid and also sulphonic acids, such as, for example, p-toluenesulphonic acid, 1,5-naphthalenedisulphonic acid or camphorsulphonic acid.

The substances shown in the following tables may be mentioned as examples of hydroxyalkyl-azolyl derivatives of the formula (I):

TABLE 1

(Ic)

| $R^4_m$ | R | X | $R^1$ | Y |
|---|---|---|---|---|
| 2,4-Cl$_2$ | H | N | Cl | —CH$_2$—CH$_2$— |
| 2,4-F$_2$ | H | N | Cl | " |
| 4-CH$_3$ | H | N | Cl | " |
| 4-CF$_3$ | H | N | Cl | " |
| 4-OCF$_3$ | H | N | Cl | " |
| 4-OCH$_3$ | H | N | Cl | " |
| 4-SCH$_3$ | H | N | Cl | " |
| 3-Cl | H | N | —S—CH$_3$ | " |
| 4-Cl | H | N | —S—C$_2$H$_5$ | " |
| 2,4,6-Cl$_3$ | " | " | Cl | —CH$_2$—CH$_2$— |
| 4-Cl | " | " | F | " |
| 4-Cl | " | CH | Cl | " |
| 4-Cl | CH$_3$ | N | Cl | " |
| 4-Cl | H | " | 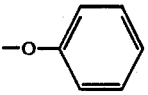 | " |
| 4-Cl | " | " | 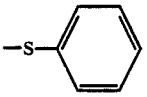 | " |
| 4-Cl | " | " | 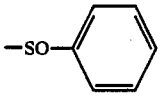 | " |
| 4-Cl | " | " | 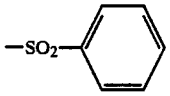 | " |
| 4-Cl | " | " | 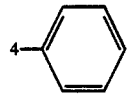 | " |
| 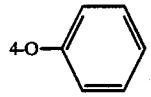 | " | " | Cl | " |
|  | " | " | Cl | " |
| 4-t.-C$_4$H$_9$ | " | " | Cl | " |
| 2-Cl, 4-CH$_3$ | " | " | Cl | " |
| — | " | " | Cl | " |
| 4-Cl | —CO—CH$_3$ | " | Cl | " |
| 4-Cl | —C$_2$H$_5$ | " | Cl | " |
| 4-F | CH$_3$ | " | F | " |
| 2,4-Cl$_2$ | H | N | Cl | —CH=CH |
| 2,4-F$_2$ | H | N | Cl | " |
| 4-CH$_3$ | H | N | Cl | " |
| 4-CF$_3$ | H | N | Cl | " |

TABLE 1-continued

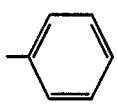

(Ic)

| R⁴ₘ | R | X | R¹ | Y |
|---|---|---|---|---|
| 4-OCF₃ | H | N | Cl | " |
| 4-OCH₃ | H | N | Cl | " |
| 4-SCH₃ | H | N | Cl | " |
| 3-Cl | H | N | —S—CH₃ | " |
| 4-Cl | H | N | —S—C₂H₅ | " |
| 2,4-Cl₂ | H | N | Cl | —C≡C— |
| 2,4-F₂ | H | N | Cl | " |
| 4-CH₃ | H | N | Cl | " |
| 4-CF₃ | H | N | Cl | " |
| 4-OCF₃ | H | N | Cl | " |
| 4-OCH₃ | H | N | Cl | " |
| 4-SCH₃ | H | N | Cl | " |
| 3-Cl | H | N | —S—CH₃ | " |
| 4-Cl | H | N | —S—C₂H₅ | " |
| 2,4,6-Cl₃ | " | " | Cl | —CH=CH— |
| 4-Cl | " | " | F | " |
| 4-Cl | " | CH | Cl | " |
| 4-Cl | CH₃ | N | Cl | " |
| 4-Cl | H | " | 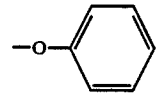 | " |
| 4-Cl | " | " | 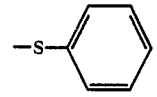 | " |
| 4-Cl | " | " | 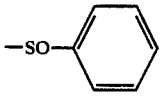 | " |
| 4-Cl | " | " | 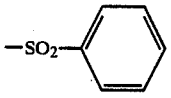 | " |
| 4-Cl | " | " |  | " |
| 4-phenyl | " | " | Cl | " |
| 4-O-phenyl | " | " | Cl | " |
| 4-t.-C₄H₉ | " | " | Cl | " |
| 2-Cl, 4-CH₃ | " | " | Cl | " |
| — | " | " | Cl | " |
| 4-Cl | —CO—CH₃ | Cl | " | " |
| 4-Cl | —C₂H₅ | " | Cl | " |
| 4-F | CH₃ | " | F | " |
| 2,4,6-Cl₃ | " | " | Cl | —C≡C— |
| 4-Cl | " | " | F | " |
| 4-Cl | " | CH | Cl | " |

TABLE 1-continued
(Ic)
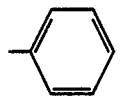
| $R^4_m$ | R | X | $R^1$ | Y |
|---|---|---|---|---|
| 4-Cl | CH$_3$ | N | Cl | " |
| 4-Cl | H | " | 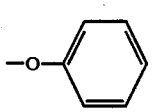 | " |
| 4-Cl | " | " | 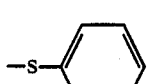 | " |
| 4-Cl | " | " | 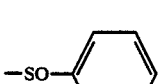 | " |
| 4-Cl | " | " | 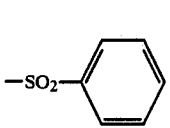 | " |
| 4-Cl | " | " | 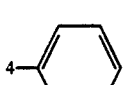 | " |
| 4-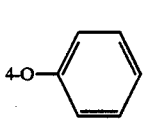 | " | " | Cl | " |
| 4-O- | " | " | Cl | " |
| 4-t.-C$_4$H$_9$ | " | " | Cl | " |
| 2-Cl, 4-CH$_3$ | " | " | Cl | " |
| — | " | " | Cl | " |
| 4-Cl | —CO—CH$_3$ | " | Cl | " |
| 4-Cl | —C$_2$H$_5$ | " | Cl | " |
| 4-F | CH$_3$ | " | F | " |

TABLE 2

| R² | R | X | R¹ | Y |
|---|---|---|---|---|
| $CH_3-\underset{\underset{CH_3}{|}}{\overset{\overset{CH_3}{|}}{C}}-$ | H | N | Cl | $-CH_2-CH_2-$ |
| $FCH_2-\underset{\underset{CH_3}{|}}{\overset{\overset{CH_3}{|}}{C}}-$ | H | N | Cl | $-CH_2-CH_2-$ |
| cyclohexyl (H) | H | N | Cl | $-CH_2-CH_2-$ |
| 1-methylcyclohexyl | H | N | Cl | $-CH_2-CH_2-$ |
| naphthyl | H | N | Cl | $-CH_2-CH_2-$ |
| 4-Cl-phenyl | H | N | Cl | $-CH_2-\underset{\underset{CH_3}{|}}{\overset{\overset{CH_3}{|}}{C}}-CH_2-CH_2-$ |
| 4-Cl-phenyl | H | N | Cl | $-CH_2-\underset{\underset{CH_3}{|}}{\overset{\overset{CH_3}{|}}{C}}-CH=CH-$ |
| 4-Cl-phenyl | H | N | Cl | $-CH_2-CH_2-CH=CH-$ |

The hydroxyalkyl-azolyl derivatives of the formula (I) to be used according to the invention and their acid addition salts are the subject of application Ser. No. 216,690 filed July 7, 1988, now pending, corresponding to German Patent Application P 3,722,794 of July 10, 1987. They can be obtained by the processes described there, by reacting (a) oxiranes of the formula

R¹, R² and Y have the abovementioned meaning, with azoles of the formula

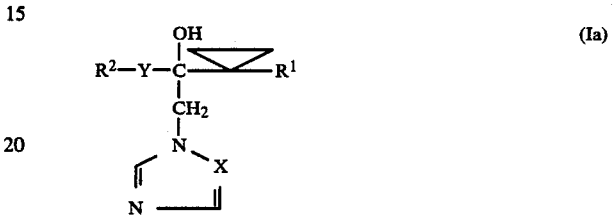

in which X has the abovementioned meaning, in the presence of an acid-binding agent, such as, for example, potassium carbonate or potassium tert.-butoxide and in the presence of a diluent, such as, for example, acetonitrile or dimethylformamide, at temperatures between 50° C. and 150° C., or (b) hydroxyalkyl-azolyl derivatives of the formula

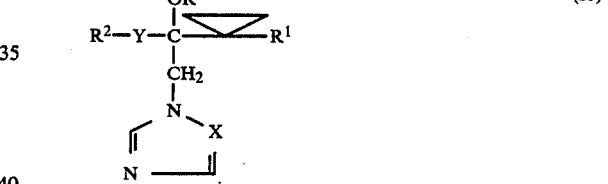

in which R¹, R², X and Y have the abovementioned meaning, with strong bases, such as, for example, amides or hydrides of alkali metals in the presence of a diluent, such as, for example, dioxane, at temperatures between 20° C. and 100° C. and reacting the alkoxides of the formula

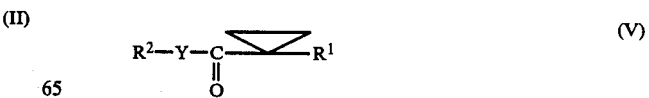

in which
R¹, R², X and Y have the abovementioned meaning and
R⁹ stands for a cationic radical of a base,
thus resulting with halogen compounds of the formula $$R^{10}-Hal \qquad (IV)$$

in which
R¹⁰ stands for alkyl or acyl and
Hal stands for halogen,
in the presence of a diluent, such as, for example, dioxane, at temperatures between 20° C. and 100° C., and if appropriate subsequently adducting an acid in a customary manner to the compounds of the formula (I) thus obtained.

The oxiranes of the formula (II) are also a subject of the above-identified patent application. They can be prepared by reacting (c) cyclopropyl ketones of the formula $$R^2-Y-\underset{\underset{O}{\|}}{C}\overline{\phantom{xx}}R^1 \qquad (V)$$

in which R¹, R² and Y have the abovementioned meaning, either (α) with dimethyloxosulphonium methylide of the formula

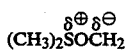   (VI)

or (β) with dimethylsulphonium methylide of the formula

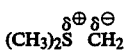   (VII)

in the presence of a diluent, or by reacting
(d) carbinols of the formula

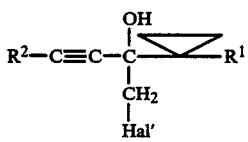   (VIII)

in which
R$^1$ and R$^2$ have the abovementioned meaning and
Hal' stands for chlorine or bromine,
with bases in the presence of a diluent.

The cyclopropyl ketones of the formula (V) required as starting material for carrying out process (c) can be prepared by reacting
(e) aldehydes of the formulae

   (IX-a)

or

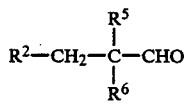   (IX-b)

in which R$^2$, R$^5$ and R$^6$ have the abovementioned meaning,
with methyl cyclopropyl ketones of the formula

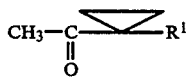   (X)

in which R$^1$ has the abovementioned meaning,
in the presence of a catalyst and in the presence of a diluent and, if appropriate, hydrogenating the cyclopropyl ketones of the formulae

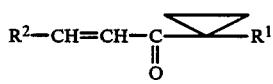   (V-a)

or

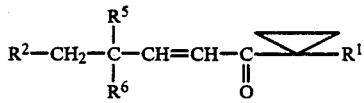   (V-b)

in which R$^1$, R$^2$, R$^5$ and R$^6$ have the abovementioned meaning,
thus resulting in the presence of a catalyst and in the presence of a diluent, or by reacting
(f) acetylenes of the formula

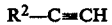   (XI)

in which R$^2$ has the abovementioned meaning,
with acid halides of the formula

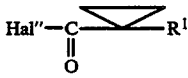   (XII)

in which
R$^1$ has the abovementioned meaning and
Hal" stands for chlorine or bromine,
in the presence of a catalyst and in the presence of a diluent.

The aldehydes of the formulae (IX-a) and (IX-b) required as starting materials for process (e) are generally known compounds of organic chemistry.

The methyl cyclopropyl ketones of the formula (X) additionally required as reaction components for carrying out process (e) are known or can be prepared by processes which are known in principle (compare Synthesis 1977, 189).

Suitable catalysts for carrying out the first step of process (e) are all reaction accelerators customary for condensations of this type. Basic substances, for example alkali metal hydroxides, such as sodium hydroxide or potassium hydroxide are preferably utilizable.

Possible diluents for carrying out the first step of process (e) are all inert organic solvents customary for reactions of this type. Alcohols, such as methanol, ethanol, isopropanol, n-butanol and tert.-butanol are preferably utilizable.

The reaction temperatures can be varied within a relatively wide range when carrying out the first step of process (e). In general, the reaction is carried out at temperatures between 0° C. and 100° C., preferably between 10° C. and 80° C.

The first step of process (e) is in general carried out under normal pressure. However, it is also possible to work at elevated or reduced pressure.

For carrying out the first step of process (e), 1 mol of aldehyde of the formula (IX) and also a catalytic amount of reaction accelerator are employed per mol of methyl cyclopropyl ketone of the formula (X). However, it is also possible to use one component or the other in an excess. Working up takes place by customary methods. In general, a procedure is used in which the reaction product produced in the solid state is filtered off with suction and is used for further reactions, if necessary after previous purification.

In the second step of process (e), the cyclopropyl ketones of the formulae (V-a) or in (V-b) are hydrogenated with hydrogen in the presence of a catalyst and a diluent. In this process, the reaction is carried out in the liquid phase using a suspended, pulverulent hydrogenation catalyst (heterogeneous) or using a catalyst complex soluble in the diluent (homogeneous). The carrying out of the hydrogenation can take place discontinuously (batchwise) or continuously as liquid-phase or trickle-bed hydrogenation in known hydrogenation reactors, such as autoclaves, autoclave cascades, tube reactors or rotating reactors. The preferred procedure is discontinuous liquid-phase hydrogenation in autoclaves at elevated pressure.

Suitable diluents for carrying out the second step of process (e) are inert organic solvents. These preferably include alcohols, such as methanol, ethanol, isopropanol or ethylene glycol; ethers, such as diethyl ether, diisopropyl ether, ethylene glycol monomethyl ether, ethylene glycol dimethyl ether, dioxane or tetrahydrofuran; saturated hydrocarbons, such as n-heptane or cyclohexane; aromatic hydrocarbons, such as toluene; and also esters, such as ethyl acetate.

For the second step of process (e), suitable hydrogenation catalysts are, for example, those which consist of metals and/or compounds of elements of the eighth subgroup of the periodic table of the elements according to Mendeleev, or contain these. Thus the metals ruthenium, rhodium, palladium, platinum, cobalt and nickel and their compounds are preferred. The metal compounds are, for example, chlorides, oxides, hydroxides and/or oxyhydrates.

The metals copper, vanadium, molybdenum, chromium and/or manganese, and compounds of these metals, can additionally be present.

The hydrogenation catalysts can consist exclusively or predominantly of hydrogen-transferring substances, but these can also be applied to support materials.

Suitable support materials for the hydrogen transferring substances are, for example: inorganic materials, such as kieselguhr, silica, aluminum oxide, silicates of alkali metals and alkaline earth metals, aluminum silicates, montmorillonite, zeolites, spinels, dolomite, kaolin, magnesium silicates, zirconium oxide, zinc oxide, calcium carbonate, silicon carbide, aluminum phosphate, boron phosphate, asbestos, activated charcoal or barium sulphate, and also organic materials, for example naturally occurring or synthetic compounds having high molecular weights such as silk, polyamides, polystyrenes, cellulose or polyurethanes. Inorganic support materials in powder form are preferred.

Supported catalysts of this type may in general contain 0.5 to 50% by weight, preferably 1 to 10% by weight, of the hydrogen-transferring substance, relative to the total amount of supported catalysts. The hydrogen-transferring substance can thus be homogeneously distributed in the support material, but catalysts in whose outer layer or on whose surface the hydrogen-transferring substance is deposited are preferred. The preparation and the shaping of the catalysts which can be used in process (e) can take place in a known manner (see, for example, Houben-Weyl, Methoden der organischen Chemie (Methods of Organic Chemistry), Volume IV, Ic, Part I, pp. 16 to 26, Georg Thieme Verlag, Stuttgart, 1980).

Preferred supported catalysts are ruthenium on charcoal, ruthenium on aluminum oxide, rhodium on charcoal, rhodium on aluminum oxide, palladium on charcoal, palladium on aluminum oxide, palladium on calcium carbonate, palladium on barium sulphate, palladium on silica, platinum on charcoal and platinum on aluminum oxide, nickel on kieselguhr, nickel on aluminum oxide and also nickel and palladium on oxide.

In the hydrogenation in a heterogeneous system, preferred hydrogenation catalysts which consist exclusively or predominantly of hydrogen-transferring substance are, for example, oxide catalysts, such as palladium oxide, platinum oxide, ruthenium oxide and/or rhodium oxide/platinum oxide according to Nishimura, furthermore metal black catalysts preparable by reduction of suitable metal salts or metal salt mixtures with alkali hydrides, alkali boranates, metal alkyls, hydrazine, formaldehyde, hydrogen or electropositive metals, such as palladium black, platinum black and rhodium black; and also spongy catalysts of the Raney type, such as Raney nickel, Raney cobalt, Raney nickel/cobalt, Raney nickel/iron, Raney nickel/copper, Raney nickel/iron/chromium, Raney nickel/palladium and Raney nickel/iron/vanadium.

In hydrogenation in a heterogeneous system, the hydrogenation catalysts are employed in the second step of process (e) in such an amount that 0.05 to 2.5, preferably 0.1 to 1% by weight, of hydrogen-transferring substance is present relative to the total weight of the reaction mixture.

For carrying out the second step of process (e), mixtures of two or more of the said hydrogenation catalysts can also be used.

The catalytic activity of the hydrogenation catalysts in general remains relatively substantial when carrying out the second step of process (e) so that these can be employed again in discontinuous procedures and can remain in use for a longer time in continuous procedures.

The reaction temperatures can be varied within a relatively wide range. In general, the reaction is carried out in the range between 0° C. and 150° C., preferably between 20° C. and 120° C.

The catalyzed heterogeneous hydrogenations in the second step of process (e) are preferably carried out at elevated pressure. In general, the hydrogenation is carried out between 1 and 150 bar, preferably between 10 and 60 bar.

In addition to the said hydrogenation catalysts of heterogeneous nature, dissolved homogeneous hydrogenation catalysts can also be employed for carrying out the second step of process (e). The selectivity of homogeneous hydrogenation catalysts, which is often higher in comparison to heterogeneous catalysts, permits the selective hydrogenation of cyclopropyl ketones of the formulae (V-a) or in (V-b) which additionally contain substituents which can be hydrogenated or are sensitive to hydrogenolysis, such as, for example, halogen on a phenyl radical. Such homogeneous hydrogenation catalysts are, for example, complexes which contain metals of the eighth sub-group of the periodic table of the elements according to Mendeleev as the central atom. The metals ruthenium, rhodium, palladium, iridium, cobalt and nickel are thus preferred. Ruthenium, rhodium and iridium are particularly preferred. Examples of metal complexes of this type are tris-(triphenylphosphine)-rhodium(I) chloride, tris-(triphenylphosphine)-ruthenium(II) chloride and bis-(triphenylphosphine)-carbonyl-iridium(I) chloride.

When using dissolved homogeneous hydrogenation catalysts, suitable diluents for carrying out the second step of process (e) are inert organic solvents. Alcohols, such as methanol, ethanol, isopropanol or ethylene glycol, furthermore hydrocarbons, such as toluene, additionally ketones, such as acetone and butanone, and also esters, such as ethyl acetate are preferably utilizable.

For the hydrogenation in a homogeneous system, the hydrogenation catalysts for carrying out the second step of process (e) are in general present in such an amount that 0.01 to 2.5 mol %, preferably 0.05 to 1.0 mol %, of hydrogenation catalyst complex is present relative to the cyclopropyl ketone of the formula (V-a) or (V-b) employed.

The reaction temperatures can also be varied within a relatively wide range when carrying out the second step of process (e). In general, the process is carried out at temperatures between 0° C. and 150° C., preferably between 20° C. and 120° C.

The hydrogenations carried out in a homogeneous system in the second step of process (e) are preferably performed under elevated pressure. In general, the hydrogenations are carried out under pressures between 1 and 150 bar, preferably between 10 and 100 bar.

In a variation, the hydrogenation in a homogeneous system in the second step of process (e) can also be carried out in such a way that molecular hydrogen is not used for the hydrogenation, but reductants are employed which are able to transfer one or more hydrogen atoms to the cyclopropyl ketone of the formula (V-a) or (V-b) in the presence of a suitable catalyst by means of a transfer hydrogenation and therefore to act as hydrogen donors. Suitable catalysts for such a transfer hydrogenation are in principle the complexes of metals of the eighth subgroup of the periodic table of the elements according to Mendeleev already described for homogeneous catalyzed hydrogenation using molecular hydrogen.

Possible hydrogen donors in this connection are primary and secondary, mono- or polyfunctional alcohols. Methanol, ethanol, n-propanol, i-propanol, n-butanol, 2-butanol, benzyl alcohol, ethylene glycol, 1,3-propanediol, 1,4-butanediol and 1,5-pentanediol are preferably utilizable. These alcohols can be used both as hydrogen donors and as solvents.

Additional hydrogen donors which can be employed in the second step of process (e) are alkali metal salts and alkaline earth metal salts of formic acid, such as sodium formate and potassium formate, and also formic acid itself. - When using a salt of formic acid, the second step of process (e) can be carried out in the form of a phase-transfer catalysis, in which the cyclopropyl ketone of the formula (V-a) or (V-b) and the hydrogenation catalyst are dissolved in a suitable inert solvent and the formate is present as an aqueous solution in a second phase. Suitable solvents in this connection are therefore those solvents which on the one hand dissolve the cyclopropyl ketone of the formula (V-a) or (V-b) and the hydrogenation catalyst, but on the other hand are not miscible with water. Solvents of this type are, for example, benzene, toluene, chlorobenzene, dichlorobenzene and methylene chloride. Possible phase-transfer catalysts are all reaction accelerators which can be employed in organic chemistry for this purpose. Tetrabutyl-ammonium bromide and methyl tridecyl-ammonium chloride (Aliquat ® 336) are preferably utilizable.

The reaction time necessary for the second step of process (e) is dependent on the reaction temperature, the hydrogen partial pressure, the intensity of mixing of the reaction mixture and on the activity and concentration of the hydrogenation catalyst. In general, the necessary reaction time is in the range from 15 minutes up to several hours. Working up in each case takes place by customary methods.

The acetylenes of the formula (XI) required as starting materials for carrying out process (f) are known or can be prepared in a simple manner by processes which are known in principle.

The acid halides of the formula (XII) required as reaction components for carrying out process (f) are also known or can be prepared by processes which are known in principle.

Suitable catalysts for carrying out process (f) are all reaction accelerators which are customary for reactions of this type. Copper salts, such as, for example, copper iodide are preferably utilizable.

Possible diluents for carrying out process (f) are all organic solvents which are customary for reactions of this type. Ethers, such as tetrahydrofuran and diethyl ether are preferably utilizable.

The reaction temperatures can be varied within a certain range when carrying out process (f). In general, the reaction is carried out at temperatures between −78° C. and +50° C., preferably between −78° C. and +40° C.

For carrying out process (f), in general 1 to 1.2 mols of acid halide of the formula (XII) and also of catalyst are employed per mol of acetylene of the formula (XI). Working up takes place by customary methods.

The dimethyl-oxo-sulphonium methylide of the formula (VI) required as a reaction component in process (c) is known (compare J. Am. Chem. Soc. 87, 1363–1364 (1965)). It is used in the above reaction in a freshly prepared state by generating it in situ by reaction of trimethyloxosulphonium iodide with sodium hydride or sodium amide, in particular with potassium tert.-butoxide or sodium methoxide, in the presence of a diluent.

The dimethylsulphonium methylide of the formula (VII) additionally required as a reaction component for process (c) is also known (compare Heterocycles 8, 397 (1977)). It is also employed in the freshly prepared state in the above reaction, by generating it in situ, for example from trimethylsulphonium halide or trimethylsulphonium methyl sulphate, in the presence of a strong base, such as, for example, sodium hydride, sodium amide, sodium methoxide, potassium tert.-butoxide or potassium hydroxide, in the presence of a diluent, such as tert.-butanol or dimethyl sulphoxide.

Suitable diluents for carrying out process (c) are inert organic solvents. Alcohols, such as tert.-butanol, ethers, such as tetrahydrofuran or dioxane, furthermore aliphatic and aromatic hydrocarbons, such as benzene, toluene or xylene, and also strongly polar solvents, such as dimethyl sulphoxide are preferably utilizable.

The reaction temperatures can be varied within a relatively wide range when carrying out process (c). In general, the reaction is carried out between 0° C. and 100° C., preferably between 10° C. and 60° C.

For carrying out process (c), in general 1 to 3 mols of dimethyloxosulphonium methylide of the formula (VI) or of dimethylsulphonium methylide of the formula (VII) are employed per mol of cyclopropyl ketone of the formula (V). The isolation of the oxiranes of the formula (II) takes place by customary methods.

The carbinols of the formula (VIII) required as starting substances for carrying out process (d) can be prepared by reacting (g) halogenoketones of the formula

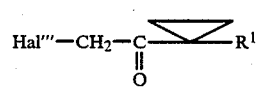
(XIII)

in which

R¹ has the abovementioned meaning and

Hal''' stands for chlorine or bromine, with acetylene salts of the formula $$R^2-C\equiv C-Me \quad (XIV)$$

in which
R² has the abovementioned meaning and
Me stands for an equivalent of a metal cation,
if appropriate in the presence of an acid-binding agent and in the presence of a diluent.

Some of the halogenoketones of the formula (XIII) required as starting materials in process (g) are known (BE-PS 879,785 and DE-OS (German Published Specification) 2,944,342). They can be prepared by reacting
h) methyl cyclopropyl ketones of the formula

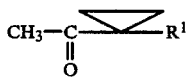  (X)

in which R¹ has the abovementioned meaning,
with chlorinating agents or brominating agents in the presence of a diluent.

Possible chlorinating agents and brominating agents for process (h) are all chlorinating and brominating reagents which are customary for reactions of this type. Sulphuryl chloride, sulphuryl bromide and bromine are preferably utilizable.

Suitable diluents for process (h) are all inert organic solvents which are customary for reactions of this type. Halogenated aliphatic hydrocarbons, such as methylene chloride, chloroform and carbon tetrachloride are preferably utilizable.

The reaction temperatures can be varied within a certain range in process (h). In general, the reaction is carried out at temperatures between −10° C. and +60° C., preferably between 0° C. and +40° C.

When carrying out process (h), the reaction is carried out under normal pressure. However, it is also possible to work at elevated or reduced pressure.

For carrying out process (h), in general a stoichiometric amount or a small excess of chlorinating or brominating agent is employed per mol of ketone of the formula (X). Working up takes place by customary methods. In general, a procedure is used in which the reaction mixture is washed successively with dilute, aqueous sodium hydrogen carbonate solution and water, then dried and concentrated.

Formula (XIV) provides a general definition of the acetylene salts required as reaction components in process (g). In this formula, R² preferably has those meanings which have already been mentioned for this radical in connection with the description of the substances of the formula (I) according to the invention. Me preferably stands for a lithium cation or for an equivalent of a Cerium(III) cation.

The acetylene salts of the formula (XIV) are known or can be prepared by processes which are known in principle.

Suitable acid binders for carrying out process (g) are all customary acid acceptors.

Possible diluents for carrying out process (g) are all customary inert organic solvents. Aromatic hydrocarbons, such as toluene, and additionally ethers, such as diethyl ether, tetrahydrofuran, tert.-butyl methyl ether and mixtures of these ethers are preferably utilizable.

The reaction temperatures can be varied within a relatively wide range when carrying out process (g). In general, the reaction is carried out at temperatures between −100° C. and +100° C., preferably between −80° C. and +50° C.

Process (g) is in general carried out under normal pressure. However, it is also possible to work at elevated or reduced pressure.

For carrying out process (g), in general 1 to 3 mols of acetylene salts of the formula (XIV) are employed per mol of halogenoketone of the formula (XIII). Working up takes place by customary methods.

Possible bases for carrying out process (d) are all organic and inorganic acid binders customarily suitable for reactions of this type. Alkali metal carbonates, such as sodium carbonate and potassium carbonate, furthermore alkali metal hydroxides, such as sodium hydroxide and potassium hydroxide, additionally alkali metal alkoxides, such as sodium methoxide and potassium methoxide, and sodium ethoxide and potassium ethoxide and also potassium tert.-butoxide, and furthermore lower tertiary alkylamines, cycloalkylamines and aralkylamines, such as triethylamine in particular are preferably utilizable.

Possible diluents for carrying out process (d) are all customary inert organic solvents. Nitriles, such as acetonitrile, furthermore aromatic hydrocarbons, such as benzene, toluene and dichlorobenzene, additionally formamides, such as dimethylformamide, and also strongly polar solvents, such as dimethyl sulphoxide and hexamethylphosphoric triamide are preferably utilizable.

The reaction temperatures can be varied within a certain range when carrying out process (d). In general, the reaction is carried out at temperatures between −20° C. and +100° C., preferably between 0° C. and 60° C.

When carrying out process (d), the reaction is generally carried out under normal pressure. However, it is also possible to work at elevated or reduced pressure.

For carrying out process (d), in general 1 to 3 mols of base are employed per mol of carbinol of the formula (VIII). Working up takes place by customary methods.

The azoles of the formula (III) additionally required as reaction components for carrying out process (a) according to the invention are generally known compounds of organic chemistry.

The hydroxyalkylazolyl derivatives of the formula (Ia) required as starting materials for process (b) according to the invention are compounds according to the invention. Their conversion into the corresponding alkoxides takes place in a generally customary manner, by reacting them at room temperature in an inert diluent, such as, for example, dixoane, with suitable strong bases, such as amides or hydrides of alkali metals, quaternary ammonium hydroxides or phosphonium hydroxides. Accordingly, R⁹ in the compounds of the formula (Ib) preferably stands for an alkali metal cation, such as a sodium or potassium cation, or for a quaternary ammonium or phosphonium cation.

The halogen compounds of the formula (IV) additionally required as starting materials for carrying out process (b) according to the invention are known or can be prepared by methods which are known in principle.

The acid addition salts of the compounds of the formula (I) can be obtained in a simple manner by customary salt formation methods, for example by dissolving a compound of the formula (I) in a suitable inert solvent and adding the acid, for example hydrochloric acid, and can be isolated in a known manner, for example by filtering off, and can be purified, if necessary, by washing with an inert organic solvent.

The compounds of the formula (I) according to the invention and their acid addition salts exhibit antimicrobial, in particular strong antimycotic, actions. They possess a very wide spectrum of antimycotic action, in particular against dermatophytes and Blastomycetes and also biphasic fungi, for example against Candida species, such as *Candida albicans*, Epidermophyton species, such as *Epidermophyton floccosum*, Aspergillus species, such as *Aspergillus niger* and *Aspergillus fumigatus*, Trichophyton species, such as *Trichophyton mentagrophytes*, Microsporon species, such as *Microsporon felineum* and also Torulopsis species, such as *Torulopsis glabrata*. The enumeration of these microorganisms in no way represents a limitation of the controllable microorganisms, but is only of illustrative character.

Examples of indications in human medicine which may be mentioned are:

Dermatomycoses and systemic mycoses produced by Trichophyton mentagrophytes and other Trichophyton species, Microsporon species and also *Epidermophyton floccosum*, Blastomycetes and biphasic fungi and also Hyphomycetes.

Indication areas in veterinary medicine which may be mentioned are: all dermatomycoses and systemic mycoses, in particular those which are produced by the abovementioned pathogens.

The present invention includes pharmaceutical preparations which contain one or more active compounds according to the invention in addition to non-toxic, inert, pharmaceutically suitable excipients or which consist of one or more active compounds according to the invention.

The present invention also includes pharmaceutical preparations in dosage units. This means that the preparations are in the form of individual portions, for example tablets, dragees, capsules, pills, suppositories and whose active compound content corresponds to a fraction or a multiple of an individual dose. The dosage units may contain, for example, 1, 2, 3 or 4 individual doses or $\frac{1}{2}$, $\frac{1}{3}$ or $\frac{1}{4}$ of an individual dose. An individual dose preferably contains the amount of active compound which is administered in one application and which usually corresponds to a whole, a half or a third or a quarter of a daily dose. Non-toxic, inert, pharmaceutically suitable excipients are taken to mean solid, semi-solid or liquid diluents, fillers or formulation auxiliaries of any type.

Preferred pharmaceutical preparations which may be mentioned are tablets, dragees, capsules, pills, granules, suppositories, solutions, suspensions and emulsions, pastes, ointments, gels, creams, lotions, powders or sprays.

Tablets, dragees, capsules, pills and granules may contain the active compound(s) in addition to the customary excipients, such as (a) fillers and extenders, for example starches, lactose, sucrose, glucose, mannitol and silica, (b) binders, for example carboxymethylcellulose, alginates, gelatine, polyvinylpyrrolidone, (c) humectants, for example glycerol, (d) disintegrants, for example agar-agar, calcium carbonate and sodium bicarbonate, (e) solution retardants, for example paraffin and (f) absorption accelerators, for example quaternary ammonium compounds, (g) wetting agents, for example cetyl alcohol, glycerol monostearate, (h) adsorption agents, for example kaolin and bentonite and (i) lubricants, for example talc, calcium stearate and magnesium stearate and solid polyethylene glycols or mixtures of the substances mentioned under (a) to (i).

The tablets, dragees, capsules, pills and granules may be provided with the customary optional opacifying agent-containing coatings and shells and can be so composed that they release the active compound(s), if appropriate with a delay, only or preferably in a certain part of the intestinal tract, it being possible, for example, for polymeric substances and waxes to be used as embedding materials.

If appropriate, the active compound(s) may also be present in microencapsulated form with one or more of the abovementioned excipients.

In addition to the active compound(s), suppositories may contain the customary water-soluble or water) insoluble excipients, for example polyethylene glycols, fats, for example cocoa fat and higher esters (for example $C_{14}$-alcohol with $C_{16}$-fatty acid) or mixtures of these substances.

Ointments, pastes, creams and gels may contain the customary excipients in addition to the active compound(s), for example animal and vegetable fats, waxes, paraffins, starches, tragacanth, cellulose derivatives, polyethylene glycols, silicones, bentonites, silica, talc and zinc oxide or mixture of these substances.

Powders and sprays may contain the customary excipients in addition to the active compound(s), for example lactose, talc, silica, aluminum hydroxide, calcium silicate and polyamide powder or mixtures of these substances, and sprays may additionally contain the customary propellants, for example chlorofluorohydrocarbons.

Solutions and emulsions may contain the customary excipients, such as solvents, solution retardants and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, maize germ oil, olive oil, castor oil and sesame oil, glycerol, glycerol formal, tetrahydrofurfuryl alcohol, polyethylene glycols and fatty acid esters of sorbitan or mixtures of these substances in addition to the active compound(s).

For parenteral administration, the solutions and emulsions may also be present in sterile and blood-isotonic form.

Suspensions may contain the customary excipients, such as liquid diluents, for example water, ethyl alcohol, propyl alcohol, suspending agents, for example ethoxylated isostearyl alcohols, polyoxyethylene sorbitol and sorbitan esters, microcrystalline cellulose, aluminum metahydroxide, bentonite, agar-agar and tragacanth or mixtures of these substances.

The said formulation forms may also contain colorants, preservatives and also odour-improving and flavor-improving additives, for example peppermint oil and eucalyptus oil and sweeteners, for example saccharine.

The therapeutically active compounds should preferably be present in the abovementioned pharmaceutical preparations in a concentration of about 0.1 to 99.5, preferably 0.5 to 95% by weight, of the total mixture.

The abovementioned pharmaceutical preparations may also contain further pharmaceutical active compounds in addition to the active compounds according to the invention.

The preparation of the abovementioned pharmaceutical preparations takes place in a customary manner by known methods, for example by mixing the active compound(s) with the excipient(s).

The present invention also includes the use of the active compounds according to the invention, and also of pharmaceutical preparations which contain one or more active compounds according to the invention, in human and veterinary medicine for the prophylaxis, amelioration and/or cure of the abovementioned diseases.

The active compounds or the pharmaceutical preparations may be administered locally, orally, parenterally, intraperitoneally and/or rectally, preferably parenterally, in particular intravenously.

In general, it has proved advantageous both in human and veterinary medicine to administer the active compound(s) according to the invention in total amounts of about 2.5 to about 200, preferably 5 to 150 mg/kg of body weight every 24 hours, if appropriate in the form of several individual doses, to obtain the desired results.

For oral administration, the active compounds according to the invention are administered in total amounts of about 2.5 to about 200, preferably 5 to 150 mg/kg of body weight every 24 hours and for parenteral administration in total amounts of about 2.5 to about 50, preferably 1 to 25 mg/kg of body weight every 24 hours.

It may be necessary, however, to deviate from the said dosages, depending upon the species and the body weight of the object to be treated, the type and severity of the disease, the type of the preparation and the administration of the medicament and also the time period or interval within which the administration takes place. Thus, in some cases it may be sufficient to manage with less than the abovementioned amount of active compound, whereas in other cases the abovementioned amount of active compound must be exceeded. The optimum dosage required in each case and the type of administration of the active compound can easily be established by one skilled in the art on the basis of his expert knowledge.

PREPARATION EXAMPLES

EXAMPLE 1

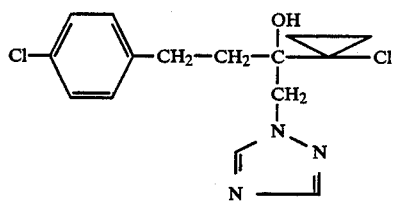
(I-1)

A solution of 13.4 g (0.05 mol) of 2-(1-chlorocyclopropyl)-2-(4-chlorophenylethyl)-oxirane in 20 ml of acetonitrile is added dropwise under a nitrogen atmosphere to a mixture of 10 g of potassium carbonate, 15 g (0.22 mol) of 1,2,4-triazole and 50 ml of acetonitrile, while the reaction mixture is heated under reflux. After completion of the addition, the reaction mixture is stirred under reflux for 8 hours more and then filtered off from the residue with suction, and the filtrate is concentrated by removing the solvent under reduced pressure. The residue which remains is taken up in ethyl acetate, and the organic phase is washed with water, dried over sodium sulphate and concentrated by removing the solvent under reduced pressure. The residue produced is chromatographed over a silica gel column using chloroform/ethanol=98:2 as eluent. After recrystallization of the product which thus remains from cyclohexane, 5.1 g (30%) of theory) of 2-(1-chlorocyclopropyl)-4-(4-chlorophenyl)-1-(1,2,4-triazol-1-yl)-butan-2-ol are obtained in the form of a solid substance of melting point 137° C.

Preparation of the starting substances:

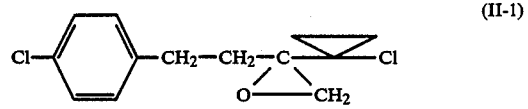
(II-1)

16 ml (0.22 mol) of dimethyl sulphide and 24.2 g (0.19 mol) of dimethyl sulphate are added to 30 ml of tert.-butanol and allowed to stand at 20° C. for 14 hours. A solution of 17 g (0.07 mol) of 1-chlorocyclopropyl 4-chlorophenylethyl ketone in 70 ml of tert.-butanol is first added dropwise to the reaction mixture with stirring and 22 g of potassium hydroxide powder are then introduced, while the temperature of the reaction mixture is kept at 20° to 30° C. The mixture is stirred at 30° C. for 3 hours more, then the dimethyl sulphide is removed under reduced pressure and the reaction mixture is then poured into 50 ml of a 1% aqueous hydrogen peroxide solution. The mixture is extracted with ethyl acetate. The organic phase is washed with water and concentrated by removing the solvent under reduced pressure after drying over sodium sulphate. In this manner, 13.4 g (75% of theory) of 2-(1-chlorocyclopropyl)-2-(4-chlorophenylethyl)-oxirane are obtained in the form of an oily product, which is reacted further without additional purification.

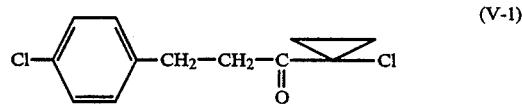
(V-1)

460 mg (0.5 mmol) of tris-triphenylphosphine rhodium chloride (=1 mol %, with reference to the reaction components) is added to a 100 ml autoclave. After purging with nitrogen, an air-free solution of 12 g (0.05 mol) of 1-chlorocyclopropyl 4-chlorophenylethenyl ketone in 40 ml of toluene is added and heated at 50° C. under a hydrogen pressure of 30 bar. The hydrogen pressure is kept between 40 and 50 bar until the absorption of gas is complete (after about 1 hour). The mixture is subsequently allowed to react for 1 hour. For working up, the solvent is removed under reduced pressure and the residue which remains is purified on silica gel using dichloromethane as the eluant. 11 g (90% of theory) of 1-chlorocyclopropyl 4-chlorophenylethyl ketone are obtained in the form of an oily product.

$^1$H-NMR (200 MHz, CDCl$_3$): δ=1.28–1.38 (m, 2H), 1.57–1.67(m, 2H), 2.84 (t, 2H), 3.15 (t, 2H), 7.08–7.29 (m, 4H).

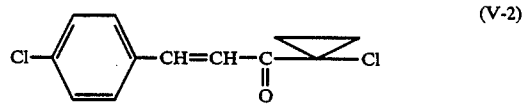
(V-2)

50 ml of water and 10 pellets of solid sodium hydroxide are added at room temperature to a mixture of 0 g (0.5 mol) of 1-chlorocyclopropyl methyl ketone, 70 g (0.5 mol) of 4-chlorobenzaldehyde and 250 ml of ethanol. The mixture is stirred at room temperature for 16 hours. The precipitated solid is then filtered off with suction. In this manner, 108.5 g (89% of theory) of 1-chlorocyclopropyl 4-chlorophenylethenyl ketone are obtained in the form of a solid substance of melting point 92° C.

EXAMPLE 2

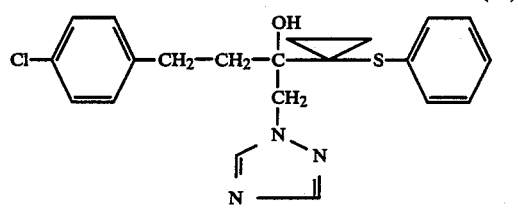
(I-2)

A solution of 25.6 g (0.1 mol) of 2-(4-chlorophenylethyl)-2-(1-phenylmercapto-cyclopropyl)-oxirane in 30 ml of acetonitrile is added dropwise under a nitrogen atmosphere to a mixture of 14 g of potassium carbonate, 21 g (0.3 mol) of 1,2,4-triazole and 70 ml of acetonitrile, while the reaction mixture is heated under reflux. After completion of the addition, the mixture is heated under reflux for 8 hours more and is then filtered from the residue with suction, and the filtrate is concentrated by removing the solvent under reduced pressure. The residue which remains is taken up in ethyl acetate/toluene, and the organic phase is washed with water, dried over sodium sulphate and concentrated by removing the solvent under reduced pressure. The residue produced is chromatographed over a silica gel column using chloroform/ethanol =99:1 as the eluant. After recrystallization of the residue which remains from cyclohexane, 11.1 g (37% of theory) of 4-(4-chlorophenyl)2-(1-phenylmercapto-cyclopropyl)-1-(1,2,4-triazol-1-yl)butan-2-ol are obtained in the form of a solid substance of melting point 137° C.

Preparation of starting substances:

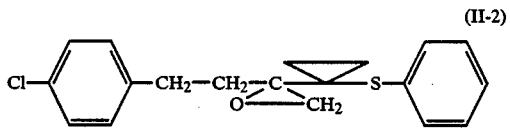
(II-2)

21 ml (0.29 mol) o& dimethyl sulphide and 32.5 g (0.26 mol) of dimethyl sulphate are added to 40 ml of tert.-butanol and allowed to stand at room temperature for 14 hours. A solution of 30 g (0.095 mol) of 4-chlorophenylethyl 1-phenylmercapto-cyclopropyl ketone in 90 ml of tert.-butanol are first added dropwise to the reaction mixture with stirring and 29.2 g of potassium hydroxide powder are then introduced, while the temperature of the reaction mixture is held at 20 to 30° C. The mixture is stirred for a further 3 hours at 30° C., then the dimethyl sulphide is removed under reduced pressure and the reaction mixture is then poured into 70 ml of a 1% strength aqueous hydrogen peroxide solution. The mixture is extracted with ethyl acetate. The organic phase is washed with water and concentrated by removing the solvent under reduced pressure after drying over sodium sulphate. In this manner, 25.6 g (82% of theory) of 2-(4-chlorophenylethyl)-2-(1-phenylmercapto-cyclopropyl)oxirane are obtained in the form of an oily product which is reacted further without additional purification.

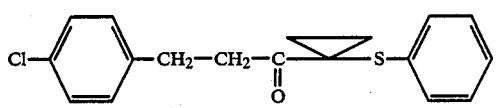
(V-3)

460 mg (0.5 mmol) o& tris-triphenylphosphinyl rhodium chloride (=1 mol %, with respect to the reaction components) is added to a 100 ml autoclave. After purging with nitrogen, an air-free solution of 15.7 g (0.05 mol) of 4-chlorophenylethenyl 1-phenylmercapto-cyclopropyl ketone in 40 ml of toluene is added and heated at 50° C. under a hydrogen pressure of 30 bar. The hydrogen pressure is kept between 40 and 50 bar until the absorption of gas is complete. The mixture is subsequently reacted for 1 hour. For working up, the solvent is removed under reduced pressure and the residue which remains is purified on silica gel using dichloromethane as the eluant. 14.2 g (90% of theory) of 4-chlorophenylethyl 1-phenylmercaptocyclopropyl ketone are obtained in the form of an oily product.

$^1$H-NMR (200 MHz, CDCl$_3$): δ=1.25–1.35 (m, 2H), 1.75–1.90 (m, 2H), 2.79 (t, 2H), 3.18 (t, 2H), 6.95–7.45 (m, 9H).

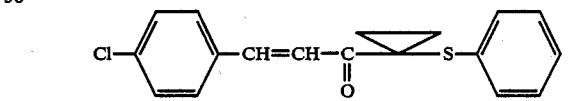
(V-4)

50 ml of water and 8 pellets of solid sodium hydroxide are added at room temperature to a mixture of 75 g (0.39 mol) of 1-phenylmercaptocyclopropyl methyl ketone, 56 g (0.39 mol) of 4-chlorobenzaldehyde and 200 ml of ethanol. The mixture is stirred at room temperature for 14 hours. The precipitated solid is then filtered off. In this manner, 120.3 g (98% of theory) of 4-chlorophenylethenyl 1-phenylmercapto-cyclopropyl ketone are obtained in the form of a solid substance.

$^1$H-NMR (200 MHz, CDCl$_3$): δ=1.32–1.41 (m, 2H), 1.87–1.95 (m, 2H), 7.05–7.84 (m, 11H).

(X-1)

A solution of 134 g (0.83 mol) of bromine in 130 ml of methylene chloride is added dropwise with stirring at 10° C. to a solution of 100 g (0.83 mol) of 5-chloropentan-2-one in 400 ml of methylene chloride. The reaction mixture is stirred for 1 hour at room temperature, then washed with water and dilute, aqueous sodium carbonate solution and dried over sodium sulphate. The mixture is concentrated by removing the solvent under reduced pressure, and the residue is taken up in 200 ml of methanol and 91.5 g (0.83 mol) of thiophenol are added at 5° C. with stirring. A mixture of 93 g of potassium hydroxide powder in 500 ml of methanol is then added dropwise. The reaction mixture is first stirred at room temperature for 2 hours and then at 40° C. for 4 hours. The mixture is subsequently concentrated by removing the solvent under reduced pressure and the residue which remains is taken up in methylene chloride. The organic solution is washed successively with water, dilute aqueous sodium carbonate solution and again with water, then concentrated under reduced pressure and then subjected to a vacuum distillation. In this manner, 76.8 g (48% of theory) of methyl 1-phenyl-mercaptocyclopropyl ketone of boiling point 155° C./20 mbar are obtained.

EXAMPLES 3 AND 4

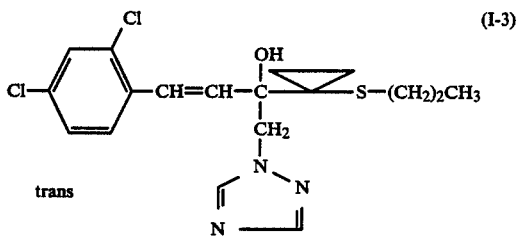

A solution of 38.2 g (0.12 mol) of 2-(2,4-dichlorophenylethenyl)-2-(1-propylmercaptocyclopropyl) oxirane in 30 ml of dimethylformamide is added dropwise under a nitrogen atmosphere and with stirring at 80° C. to a mixture of 24 g (0.35 mol) of 1,2,4-triazole, 2.7 g (0.02 mol) of potassium tert.-butoxide and 50 ml of dimethylformamide. The mixture is stirred at 80° C. for 6 hours, then the solvent is removed under reduced pressure, and the residue is taken up in ethyl acetate/toluene, washed with water, dried over sodium sulphate and concentrated under reduced pressure. The residue which remains is chromatographed on silica gel using chloroform as the eluant. In this manner, 12.1 g (26% of theory) of trans-4-(2,4-dichlorophenyl)-2-(1-propylmercaptocyclopropyl)1-(1,2,4-triazol-1-yl)-but-3-en-2-ol are obtained in the form of an oily product.

$^1$H-NMR (200 MHz, CDCl$_3$): δ=0.75–1.65 (m, 9H), 2.63 (t, 2H), 4.62 (d, 1H), 4.73 (d, 1H), 6.30 (d, 1H), 6.90 (d, 1H), 7.12–7.42 (m, 3H), 7.90 (s, 1H), 8.17 (s, 1H).

1.8 g (4% of theory) of cis-4-(2,4-dichlorophenyl)-2-(1-propylmercaptocyclopropyl)-1-(1,2,4-triazol-1-yl)-but-3-en-2-ol are additionally isolated (compound I-4).

$^1$H-NMR (200 MHz, CDCl$_3$): δ=0.75–1.10 (m, 7H), 1.50 (sex, 2H), 2.40 (t, 2H), 4.35–4.53 (m, 3H), 5.97 (d, 1H), 7.00 (d, 1H), 7.20–7.44 (m, 3H), 7.92 (s, 1H), 8.13 (s, 1H).

Preparation of starting substances:

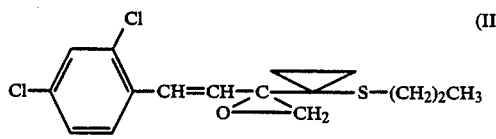

30 ml (0.41 mol) of dimethyl sulphide and 43.5 g (0.35 mol) of dimethyl sulphate are added to 60 ml of tert.-butanol and allowed to stand at room temperature for 14 hours. A solution of 40 g (0.13 mol) of 2,4-dichlorophenylethenyl 1-propylmercaptocyclopropyl ketone in 120 ml of tert.-butanol is first added to the reaction mixture with stirring and 39.1 g of potassium hydroxide powder are then introduced, while keeping the temperature of the reaction mixture at 20° to 30° C. The mixture is stirred at 30 C. for 3 hours more, then the dimethyl sulphide is removed under reduced pressure and the reaction mixture is then poured into 70 ml of a 1% strength aqueous hydrogen peroxide solution. The mixture is extracted with ethyl acetate. The organic phase is washed with water and concentrated by removing the solvent under reduced pressure after drying over sodium sulphate. In this manner, 38.2 g (91% of theory) of 2-(2,4-dichlorophenylethenyl)-2-(1-propylmercaptocyclopropyl)-oxirane are obtained in the form of an oily product, which is reacted further without additional purification.

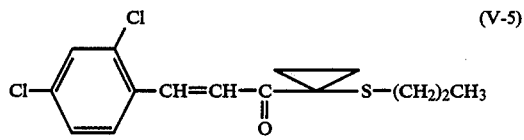

5 pellets of solid sodium hydroxide are added at room temperature to a mixture of 41.7 g (0.26 mol) of 1-acetyl-1-propylmercapto-cyclopropane, 46 g (0.26 mol) of 2,4-dichlorobenzaldehyde, 130 ml of ethanol and 30 ml of dichloromethane. The mixture is stirred for 14 hours at room temperature. 50 ml of water are added, and the oil phase is separated off and taken up in dichloromethane. The organic phase is washed with water, dried over sodium sulphate and concentrated by removing the solvent under reduced pressure. In this manner, 80 g (97% of theory) of 2,4-dichlorophenylethenyl 1-propylmercaptocyclopropyl ketone (cis/trans isomers) are obtained in the form of an oily product.

$^1$H-NMR (200 MHz, CDCl$_3$): δ=0.95 (t, 3H), 1.19–1.29 (m, 2H), 1.50–1.70 (m, 4H), 2.57 (t, 2H), 7.20–7.95 (m, 5H).

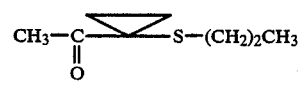

A solution of 134 g (0.83 mol) of bromine in 130 ml of methylene chloride is added dropwise at 10° C. with stirring to a solution of 100 g (0.83 mol) of 5-chloropentan-2-one in 400 ml of methylene chloride. The reaction mixture is stirred at room temperature for 1 hour, then washed with water and dilute, aqueous sodium carbonate solution and dried over sodium sulphate. The mixture is concentrated by removing the solvent under reduced pressure, and the residue is taken up in 200 ml of methanol and 63 g (0.83 mol) of n-propylmercaptan are added at 5° C. with stirring. A mixture of 93 g of potassium hydroxide powder in 500 ml of methanol are then added dropwise. The reaction mixture is first stirred at room temperature for 2 hours and then at 40° C. for 4 hours. The mixture is subsequently concentrated by removing the solvent under reduced pressure and the residue which remains is taken up in methylene chloride. The organic solution is washed successively with water, dilute aqueous sodium hydroxide solution and again with water, then concentrated under reduced pressure and then subjected to a vacuum distillation. In this manner, 42 g (32% of theory) of 1-acetyl-1-propylmercapto-cyclopropane of boiling point 107° C./20 mbar are obtained.

EXAMPLE 5

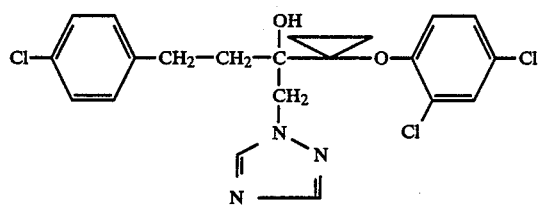
(I-5)

4-(4-Chlorophenyl)-2-[1-(2,4-dichlorophenoxy)cyclopropyl]-1-(1,2,4-triazol-1-yl)-butan-2-ol is also obtained in the form of an oily product by the previously indicated methods.

$^1$H-NMR (200 MHz, CDCl$_3$): δ=0.25–0.45 (m, 2H), 0.67–0.83 (m, 1H), 0.83–1.05 (m, 1H), 1.80–2.15 (m, 2H), 2.70–2.90 (m, 1H), 2.90–3.13 (m, 1H), 4.16 (s, 1H), 4.38 (d, 1H), 4.70 (d, 1H), 7.00–7.40 (m, 7H), 8.02 (s, 1H), 8.38 (s, 1H).

The substances shown in the following Table 3 were also obtained by the methods which have been described in the previously indicated examples.

TABLE 3

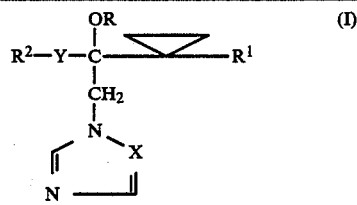
(I)

| Compound No. | R$^2$ | Y | R$^1$ | R | X | Characterization by |
|---|---|---|---|---|---|---|
| I-6 | 4-Cl-C$_6$H$_4$ | —CH$_2$—CH$_2$— | —SCH$_3$ | H | N | M.p. = 115° C. |
| I-7 | 2,4-Cl$_2$-C$_6$H$_3$ | —CH$_2$—CH$_2$— | —S(CH$_2$)$_2$CH$_3$ | H | N | NMR spectrum |
| I-8 | 4-Cl-C$_6$H$_4$ | —CH$_2$—CH$_2$— | —SCH(CH$_3$)$_2$ | H | N | NMR spectrum |
| I-9 | 2,4-Cl$_2$-C$_6$H$_3$ | —CH$_2$—CH$_2$— | —SC$_2$H$_5$ | H | N | NMR spectrum |
| I-10 | 4-Cl-C$_6$H$_4$ | —CH$_2$—CH$_2$— | —S—CH$_2$—C$_6$H$_5$ | H | N | NMR spectrum |
| I-11 | 2,4-F$_2$-C$_6$H$_3$ | —CH$_2$—CH$_2$— | Cl | H | N | NMR spectrum |
| I-12 | 4-F-C$_6$H$_4$ | —CH$_2$—CH$_2$— | Cl | H | N | NMR spectrum |
| I-13 | 4-Cl-C$_6$H$_4$ | —CH=CH— | —SCH$_3$ | H | N | NMR spectrum |

TABLE 3-continued $$R^2-Y-\underset{\underset{\underset{N\phantom{X}}{\overset{\displaystyle N-X}{|}}}{\overset{\displaystyle CH_2}{|}}}{\overset{\displaystyle OR}{C}}-R^1 \quad (I)$$

| Compound No. | R² | Y | R¹ | R | X | Characterization by |
|---|---|---|---|---|---|---|
| I-14 | 4-Cl-C₆H₄− | −CH=CH− (trans) | −S−C₆H₅ | H | N | NMR spectrum |
| I-15 | 4-Cl-C₆H₄− | −CH=CH− (cis) | −S−C₆H₅ | H | N | NMR spectrum |
| I-16 | 2,4-Cl₂-C₆H₃− | −CH=CH− | −SC₂H₅ | H | N | NMR spectrum |
| I-17 | 4-Cl-C₆H₄− | −CH₂−C(CH₃)₂−CH₂−CH₂− | Cl | H | N | NMR spectrum |
| I-18 | 4-CF₃-C₆H₄− | −CH₂−CH₂− | Cl | H | N | NMR spectrum |
| I-19 | 2-Cl-C₆H₄− | −CH₂−CH₂− | Cl | H | N | M.p. 100° C. |
| I-20 | 4-CH₃-C₆H₄− | −CH₂−CH₂− | Cl | H | N | M.p. 118° C. |
| I-21 | 4-Br-C₆H₄− | −CH₂−CH₂− | Cl | H | N | M.p. 132° C. |
| I-22 | 2,4-Cl₂-C₆H₃− | −CH₂−CH₂− | Cl | H | N | M.p. 108° C. |
| I-23 | C₆H₅− | −CH₂−CH₂− | Cl | H | N | M.p. 94° C. |
| I-24 | 4-CF₃O-C₆H₄− | −CH₂−CH₂− | Cl | H | N | NMR spectrum |

TABLE 3-continued $$R^2-Y-\underset{\underset{N}{\overset{|}{C}}}{\overset{OR}{\underset{CH_2}{\overset{|}{\bigtriangleup}}}}R^1 \quad (I)$$

| Compound No. | R² | Y | R¹ | R | X | Characterization by |
|---|---|---|---|---|---|---|
| I-25 | 4-biphenylyl | —CH₂—CH₂— | Cl | H | N | M.p. 128° C. |
| I-26 | 3-bromo-4-fluorophenyl | —CH₂—CH₂— | Cl | H | N | NMR spectrum |
| I-27 | 3-trifluoromethylphenyl | —CH₂—CH₂— | Cl | H | N | NMR spectrum |
| I-28 | 4-methylphenyl | —CH=CH— | Cl | H | N | M.p. 106° C. |
| I-29 | 2,4-dichlorophenyl | —CH=CH— | Cl | H | N | M.p. 112° C. |
| I-30 | 4-bromophenyl | —CH=CH— | Cl | H | N | M.p.: 130° C. |
| I-31 | 2-chlorophenyl | —CH=CH— | Cl | H | N | M.p.: 133° C. |
| I-32 | phenyl | —CH=CH— | Cl | H | N | M.p.: 90° C. |
| I-33 | 4-trifluoromethoxyphenyl | —CH=CH— | Cl | H | N | M.p.: 67° C. |
| I-34 | 3-bromo-4-fluorophenyl | —CH=CH— | Cl | H | N | M.p.: 126° C. |

TABLE 3-continued

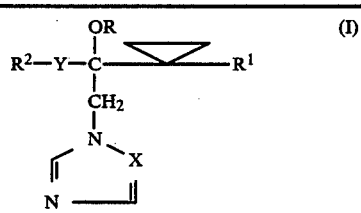

| Compound No. | R² | Y | R¹ | R | X | Characterization by |
|---|---|---|---|---|---|---|
| I-35 | 3-CF₃-C₆H₄- | —CH=CH— | Cl | H | N | NMR spectrum |
| I-36 | 3,4-Cl₂-C₆H₃- | —CH=CH— | Cl | H | N | NMR spectrum |
| I-37 | 3-F-C₆H₄- | —CH=CH— | Cl | H | N | NMR spectrum |
| I-38 | (CH₃)₃C— | —CH=CH— | Cl | H | N | M.p. 74° C. |
| I-39 | C₆H₁₁- | —CH=CH— | Cl | H | N | M.p. 95° C. |
| I-40 | C₆H₁₁- | —CH₂—CH₂— | Cl | H | N | M.p. 67° C. |
| I-41 | 4-CF₃S-C₆H₄- | —CH=CH— | Cl | H | N | R_f: 0.32 (CH₂Cl₂/CH₃COOC₂H₅ 4:1) |
| I-42 | 2-F-4-Cl-C₆H₃- | —CH=CH— | Cl | H | N | M.p. 92° C. |
| I-43 | 2-Cl-6-F-C₆H₃- | —CH=CH— | Cl | H | N | M.p. 1:12° C. |
| I-44 | 3-F-C₆H₄- | —CH₂—CH₂— | Cl | H | N | R_f: 0.34 (CH₂Cl₂/CH₃COOC₂H₅ 4:1) |

TABLE 3-continued $$R^2-Y-\underset{\underset{CH_2}{|}}{\overset{\overset{OR}{|}}{C}}-\triangle-R^1 \quad (I)$$
$$\underset{N\equiv\!\!\!=\!\!\!}{\overset{|}{N}}\!\!-\!\!X$$

| Compound No. | R² | Y | R¹ | R | X | Characterization by |
|---|---|---|---|---|---|---|
| I-45 | 2-Cl-3-F-phenyl | —CH=CH— | Cl | H | N | M.p.: 112° C. |
| I-46 | 3,4-diCl-phenyl | —CH=CH— | Cl | H | N | M.p.: 137° C. |
| I-47 | 2-naphthyl | —CH=CH— | Cl | H | N | M.p.: 114–116° C. |
| I-48 | 2-Cl-3-F-phenyl | —CH₂—CH₂— | Cl | H | N | M.p.: 84° C. |
| I-49 | 2-Cl-6-F-phenyl | —CH₂—CH₂— | Cl | H | N | M.p.: 72° C. |
| I-50 | 4-(CF₃S)-phenyl | —CH₂—CH₂— | Cl | H | N | M.p.: 88° C. |
| I-51 | 4-O₂N-phenyl | —CH₂—CH₂— | Cl | H | N | M.p.: 105° C. |
| I-52 | 4-Cl-phenyl | —CH=CH— | Cl | H | N | M.p.: 122° C. |
| I-53 | 4-CH₃O-phenyl | —CH₂—CH₂— | Cl | H | N | M.p.: 90° C. |
| I-54 | 2-naphthyl | —CH₂—CH₂— | Cl | H | N | M.p.: 134° C. |

TABLE 3-continued $$R^2-Y-\underset{\underset{\displaystyle CH_2}{|}}{\overset{\overset{\displaystyle OR}{|}}{C}}\!\!\!-\!\!\!\triangle\!\!\!-R^1 \qquad (I)$$
$$\underset{N\!=\!\!\!=\!\!\!=\!\!}{\overset{}{\underset{}{N-X}}}$$

| Compound No. | R² | Y | R¹ | R | X | Characterization by |
|---|---|---|---|---|---|---|
| I-55 | 4-(F₂C-O-CF₂-O)-phenyl | —CH=CH— | Cl | H | N | Oil |
| I-56 | 1-naphthyl | —CH₂—CH₂— | Cl | H | N | M.p.: 102° C. |
| I-57 | 4-chloro-2-fluorophenyl | —CH₂—CH₂— | Cl | H | N | M.p.: 112° C. |
| I-58 | 4-chlorophenyl | —C≡C— | Cl | H | N | M.p.: 112° C. |
| I-59 | 2-chlorophenyl | —C≡C— | Cl | H | N | Oil |
| I-60 | phenyl | —C≡C— | Cl | H | N | M.p.: 116–118° C. |
| I-61 | 4-(F₃CO)-phenyl | —CH₂—CH₂— | 4-Cl-phenyl | H | N | M.p.: 132° C. |
| I-62 | 4-Cl-phenyl | —CH₂—CH₂— | 4-Cl-phenyl | H | N | M.p.: 123° C. |
| I-63 | 4-(F₃CO)-phenyl | —CH=CH— | 4-Cl-phenyl | H | N | M.p.: 82° C. |
| I-64 | 4-Cl-phenyl | —CH=CH— | 4-Cl-phenyl | H | N | M.p.: 146° C. |

Use Examples

The compounds indicated below are employed as comparison substances in the following examples:

(known from EP-OS 0,180,850)

EXAMPLE A

Antimycotic in vitro activity

Experimental description:
The in vitro tests were carried out in the serial dilution test using inocula of microorganisms of approximately $5 \times 10^3$ to $10^4$ microorganisms/ml of substrate. The nutrient medium used was (a) for dermatophytes and Blastomycetes: Sabouraud's test medium (b) for yeasts: meat extract/dextrose broth.

The incubation temperature was 28° C. to 37° C., and the incubation period was 24 to 96 hours with yeasts and 96 hours with dermatophytes and Blastomycetes.

In this test, for example, the compounds according to the invention I-1, I-3, I-6, I-8, I-9, I-10, I-12, I-13, I-16, I-17, I-19, I-20, I-22, I-23, I-24, I-25, I-28, I-29, I-30, I-31, I-32, I-33, I-34, I-38 and I-39 show a better antimycotic activity than the compounds (A) and (B) known from the prior art.

TABLE A

Antimycotic in vitro activity
MIC values in μg/ml of nutrient medium

| Active compound | Tricho- phyton mentagr. | Micro- sporum canis | Candida albi- cans | Torul- opsis gla- brata | Asper- gillus fumi- gatus |
|---|---|---|---|---|---|
| (A) (known) | >64 | — | >64 | — | >64 |
| (B) (known) | 64 | — | 16 | 64 | >64 |
| Compounds according to Preparation Example | | | | | |
| I-1 | <1 | <1 | 2 | <1 | <1 |
| I-3 | 8 | — | 4 | 4 | 16 |
| I-6 | <1 | 2 | 4 | 16 | <1 |
| I-8 | 2 | — | 8 | 32 | 4 |
| I-9 | 8 | — | 4 | 16 | 16 |
| I-10 | <1 | 8 | 2 | 4 | 64 |
| I-12 | <1 | 4 | 8 | 32 | <1 |
| I-13 | <1 | 4 | 2 | 2 | <1 |
| I-16 | <1 | <1 | 8 | <1 | 4 |
| I-17 | 2 | — | <1 | 2 | 4 |
| I-19 | <1 | 2 | 4 | 16 | 2 |
| I-20 | <1 | 2 | 4 | 2 | <1 |
| I-22 | <1 | 4 | 2 | 2 | <1 |
| I-23 | <1 | 2 | 4 | 8 | <1 |
| I-24 | <1 | 4 | 16 | 4 | <1 |
| I-25 | <1 | 2 | <1 | 2 | <1 |
| I-28 | <1 | <1 | <1 | <1 | <1 |
| I-29 | <1 | <1 | 16 | 8 | <1 |
| I-30 | <1 | <1 | 2 | 4 | <1 |

TABLE A-continued

Antimycotic in vitro activity
MIC values in μg/ml of nutrient medium

| Active compound | Tricho- phyton mentagr. | Micro- sporum canis | Candida albi- cans | Torul- opsis gla- brata | Asper- gillus fumi- gatus |
|---|---|---|---|---|---|
| I-31 | <1 | 4 | 8 | 8 | 2 |
| I-32 | <1 | 4 | 4 | 8 | 2 |
| I-33 | <1 | <1 | 8 | <1 | <1 |
| I-34 | 2 | — | 4 | 4 | <1 |
| I-38 | <1 | 4 | 4 | 4 | 8 |
| I-39 | 2 | — | 16 | 16 | 2 |

EXAMPLE B

Antimycotic in vivo activity (oral) in mouse candidiasis

Experimental description:
Mice of the SPF-CF1 type were intravenously inoculated with $1-2 \times 10^6$ logarithmically growing Candida cells, suspended in physiological saline solution. One hour before and seven hours after the inoculation, the animals are in each case orally treated with 10–100 mg/kg of body weight of the preparation.

Result:
Untreated animals died 3 to 6 days post infection. The survival rate on the 6th day post infection was about 5% in untreated control animals.

In this test, for example, the compounds (I-1), (I-6), (I-13), (I-29), (I-30), (I-33) and (I-34) according to the invention show a better action than the compounds (A) and (B) known from the prior art.

TABLE B

Antimycotic in vivo action (oral) in mouse candidiasis

| Active compound | Action |
|---|---|
| (A) (known) | n.a. |
| (B) (known) | n.a. |
| Compound according to Preparation Example | |
| (I-1) | +++ |
| (I-6) | +++ |
| (I-13) | +++++ |
| (I-29) | +++ |
| (I-30) | +++++ |
| (I-33) | +++++ |
| (I-34) | +++ |

Explanation of symbols:
+++++ = very good action = 90% survival on the 6th day post infection
++++ = good action = 80% survival on the 6th day post infection
+++ = action = 60% survival on the 6th day post infection
++ = weak action = 40% survival on the 6th day post infection
+ = trace action = under 40% survival on the 6th day post infection
n.a. = no difference to untreated infection controls

Example C/Formulations

| 1. Solution: | |
|---|---|
| Active compound according to formula (I) | 10 g |
| Alcohol, pure (96% strength) | 300 g |
| Isopropyl myristrate | 526 g |
| | 836 g |
| 2. Cream: | |
| Active compound according to formula (I) | 10 g |
| Aralcel 60 | 20 g |
| (sorbitan monostearate) | |
| Tween 60 | 15 g |
| (polyoxyethylene (2) sorbitan monostearate) | |
| Spermaceti, synthetic | 30 g |
| (mixture of esters of saturated $C_{14}$-$C_{18}$ fatty acids and $C_{14}$-$C_{18}$ fatty alcohols) | |

-continued

| | |
|---|---|
| Lanette O | 100 g |
| Eutanol G (2-octyl-dodecanol) | 135 g |
| Benzyl alcohol | 10 g |
| Water, demineralized | 680 g |
| | 1,000 g |

It is understood that the specification and examples are illustrative but not limitative of the present invention and that other embodiments within the spirit and scope of the invention will suggest themselves to those skilled in the art.

What is claimed is:

1. A method of combating mycoses in a patient in need thereof which comprises administering to such patient an antimycotically effective amount of a hydroxyalkyl-azolyl derivative of the formula

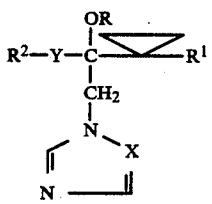

in which
R¹ is fluorine, chlorine, bromine or phenyl which is optionally mono-substituted by chlorine.
R² is alkyl with 1 to 4 carbon atoms, which is optionally mono-or di-substituted by methoxy, or is cycloalkyl having 3 to 7 carbon atoms, which is optionally mono-substituted by methyl, or is naphthyl, or the radical of the formula

wherein
R⁴ is fluorine, chlorine, bromine, methyl, ethyl, isopropyl, tert.-butyl, methoxy, trifluoromethyl, trifluoromethoxy, trifluoromethylthio, phenyl, phenoxy or nitro, and
m is 0,1,2 or 3, or
R² is the radical of the formula

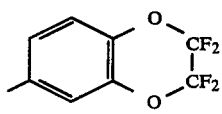

Y represents the groupings —CH₂—CH₂—, —CH=CH—, —C≡C— or

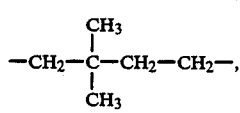

or an acid addition salt thereof.

2. The method according to claim 1, wherein such compound is 2-(1-chlorocyclopropyl)-4-(4-chlorophenyl)-1-(1,2,4-triazol-1-yl)-butan-2-ol of the formula

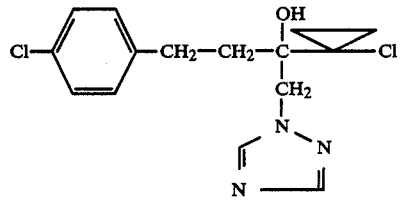

or an acid salt thereof.

3. The method according to claim 1, wherein such compound is 4-(4-chlorophenyl)-2-(1-methylmercaptocyclopropyl)-1-(1,2,4-triazol-1-yl)-butan-2-ol of the formula

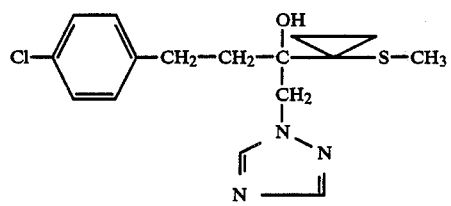

4. The method according to claim 1, wherein such compound is 4-(4-chlorophenyl)-2-(1-methylmercaptocyclopropyl)-1-(1,2,4-triazol-1-yl)-but-3-en-2-ol of the formula

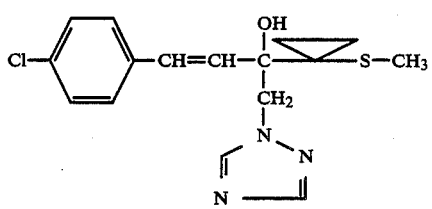

or an acid addition salt thereof.

5. The method according to claim 1, wherein such compound is 4-(4-bromophenyl)-2-(1-chlorocyclopropyl)-1-(1,2,4-triazol-1-but-3-en-2-ol of the formula

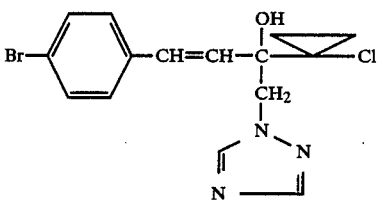

or an acid addition salt thereof.

6. The method according to claim 1, wherein such compound is 4-(4-trifluoromethoxyphenyl)-2-(1-chlorocyclopropyl)-1-(1,2,4-triazol-1-yl)-but-3-en-2-ol of the formula

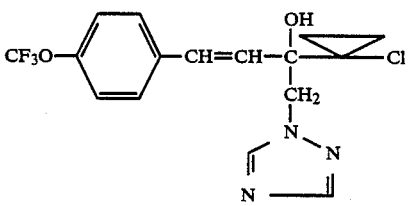

or an acid addition salt thereof.

* * * * *

UNITED STATES PATENT AND TRADEMARK OFFICE
CERTIFICATE OF CORRECTION

PATENT NO. : 4,925,865
DATED : May 15, 1990
INVENTOR(S) : Klaus Stroech, et al

It is certified that error appears in the above-identified patent and that said Letters Patent is hereby corrected as shown below:

Col. 43, lines 20-27     Delete bottom right of formula and substitute $$-- \diagdown_{\underset{\text{N}}{\big|}} --$$

Col. 43, line 31     Delete "." and substitute --,--

Col. 43, line 53     After formula insert --and--
Col. 44, line 24     After formula insert --or an acid addition salt thereof.--

Col. 44, line 42     After "triazol-1-" insert --yl)-.--

Signed and Sealed this

Sixteenth Day of June, 1992

Attest:

DOUGLAS B. COMER

Attesting Officer     Acting Commissioner of Patents and Trademarks